(12) United States Patent
Demars et al.

(10) Patent No.: US 6,294,180 B1
(45) Date of Patent: Sep. 25, 2001

(54) COSMETIC AND/OR DERMATOLOGICAL POWDER, PROCESS FOR ITS PREPARATION AND ITS USES

(75) Inventors: Gwenaeelle Demars, Bourg la Reine; Sandrine Koely, Antony, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/436,030

(22) Filed: Nov. 8, 1999

(30) Foreign Application Priority Data

Nov. 6, 1998 (FR) .................................................. 98 14029

(51) Int. Cl.⁷ ............................ A61K 7/00; A61K 7/035; A61K 31/74; A61K 7/14
(52) U.S. Cl. ..................... 424/401; 424/69; 424/78.03; 424/78.31; 424/486; 424/489
(58) Field of Search ................................ 424/63, 401, 65, 424/69, 486, 61, 489, 464, 465, 78.03, 78.31, 502; 524/47; 514/844, 937

(56) References Cited

U.S. PATENT DOCUMENTS

| 5,063,050 | * | 11/1991 | Verdon et al. | 424/63 |
|---|---|---|---|---|
| 5,223,559 | * | 6/1993 | Arraudeau et al. | 524/47 |
| 5,510,107 | | 4/1996 | Lecomte et al. . | |
| 5,939,079 | * | 8/1999 | Le Royer et al. | 424/401 |

FOREIGN PATENT DOCUMENTS

| 1.600.591 | 7/1970 | (FR) . |
|---|---|---|
| 96/22073 | 7/1996 | (WO) . |
| 96/38127 | 12/1996 | (WO) . |
| 98/19652 | 5/1998 | (WO) . |

* cited by examiner

Primary Examiner—Thurman K. Page
Assistant Examiner—Blessing Fubara
(74) Attorney, Agent, or Firm—Oblon, Spivak, McClelland, Maier & Neustadt, P.C.

(57) ABSTRACT

A cosmetic or dermatological powder, which comprises (i) from 5 to 60% by weight, relative to the total weight of the powder, of at least one starch modified by pregelatinization, oxidation, crosslinking, esterification or a combination thereof, (ii) from 30 to 90% by weight, relative to the total weight of the powder, of an oily phase comprising at least one oil, and (iii) at least one electrolyte, wherein the oily phase/starch weight ratio is $\geq 1$.

31 Claims, No Drawings

COSMETIC AND/OR DERMATOLOGICAL POWDER, PROCESS FOR ITS PREPARATION AND ITS USES

BACKGROUND OF THE INVENTION

1. Field of the Invention

The present invention relates to a cosmetic or dermatological powder containing at least one electrolyte, to a process for its manufacture and to a composition containing it. More particularly, the invention relates to the use of the powder or of the composition for the care and/or treatment of the skin, mucous membranes and/or the scalp, as well as for the treatment of skin disorders.

2. Description of the Background

Compositions containing electrolytes (inorganic and organic salts), which are useful for their beneficial effects on the skin, are known in cosmetics and dermatology. Certain electrolytes make it possible, in particular, to treat problems of sensitive skin and the pathological or physiological disorders associated with the release of substance P and/or TNF-alpha (Tumor Necrosis Factor-alpha) and in particular to treat sensitive skin, skin disorders and skin diseases. Such compositions are described, for example, in EP 0 737 471, EP 0 770 392 and EP 0 775 492.

Moreover, it is known that the incorporation of electrolytes into cosmetic or dermatological compositions containing water poses problems, because of the incompatibility of electrolytes with certain constituents usually employed in such compositions. Thus, for example, electrolytes are incopatible with the neutralized caboxyvinyl polymers usually used as gelling agents, since they "break" the emulsion and liquify it. As a result, compositions containing caboxyvinyl polymers and electrolytes lack consistency, which is counter to the result desired when a gelling agent is used.

It has now been found, unexpectedly, that it is possible to prepare a composition which is free of the drawbacks of the compositions of the prior art by incorporating electrolytes into an anhydrous powder containing a modified starch and which can contain at least one fatty substance.

Admittedly, JP-A-7/206,663 describes a bath powder containing inorganic salts, sugars and fatty substances. However, this powder has the drawback of being sensitive to moisture and bacteriological contamination. A need therefore continues to exist for salt-containing cosmetic compositions of improved pathological and physiological properties which are less sensitive to water and bacteriological contamination.

SUMMARY OF THE INVENTION

Accordingly, one object of the present invention is to provide a cosmetic composition which contains an electrolyte salt but which at the same time is stable at therapeutic concentrations of salt and is less sensitive to moisture and bacteriological contamination.

Briefly, this object and other objects of the present invention as hereinafter will become more readily apparent can be attained by a cosmetic or dermatological powder, which comprises, (i) from 5 to 60% by weight, relative to the total weight of the powder, of at least one starch modified by pregelatinization, oxidation, crosslinking, esterification or a combination thereof, (ii) from 30 to 90% by weight, relative to the total weight of the powder, of an oily phase comprising at least one oil, and (iii) at least one electrolyte, wherein the oily phase/starch weight ratio is $\geq 1$.

DETAILED DESCRIPTION OF THE PREFERRED EMBODIMENTS

The term "powder" in this invention means a solid substance divided into very fine, homogeneous particles or grains. The powder of the invention is preferably free of protein.

In one specific embodiment of the invention the powder comprises from 5 to 50% by weight, relative to the total weight of the powder, of at least one modified starch, from 0.1 to 40% by weight, relative to the total weight of the powder, of at least one electrolyte, and from 50 to 90% by weight, relative to the total weight of the powder, of an oily phase comprising at least one oil.

The cosmetic or dermatological powder of the invention comprises an oily phase fixed in the modified starch. This powder in particular has the advantages of being able to contain a large amount of electrolyte, of being applicable to any skin type without leaving a greasy effect, despite the large amount of oil, of being easy and quick to use, of penetrating the skin without leaving a visible film, of retaining the moisturizing or nourishing properties of the fatty substances and of not requiring the addition of a liquid such as water since it can be used in its existing form. In addition, the desired amount can be taken-up easily. Moreover, the powder of the invention is not sensitive to moisture or to bacteriological contamination. In addition, since this powder can be obtained without any emulsifier and since it keeps well, it is possible to avoid the addition of emulsifiers and/or preserving agents, and thus to obtain a powder which is much less of an irritant than the conventional skin care products.

In addition, the cosmetic product of the invention allows the incorporation of compounds therein which have different physicochemical properties. This product can thus comprise detergents. This makes it possible, in particular, to cleanse the skin while at the same time moisturizing and nourishing the skin. In fact, the present invention represents a significant contribution to the art since it provides a multipurpose cosmetic or dermatological product which is not specific to one skin type.

Another advantage of the powder of the invention is that compounds known to be sensitive to water and/or to oxidation, such as vitamins including vitamin C, vitamin A and esters thereof and enzymes, can be incorporated therein. In this medium, these compounds will keep for a long time and thus will not lose their activity over time.

Finally, the powder of the invention has the further advantage of also being able to be incorporated into a cosmetic and/or dermatological composition, such as a lotion, a W/O or O/W emulsion, or a triple emulsion. A composition is thus obtained which, although containing a large amount of electrolyte(s), remains stable even in the presence of compounds with which the electrolytes are usually incopatible.

An aspect of the present invention is also a cosmetic and/or dermatological composition, which comprises at least one powder as defined above.

The powder of the invention has a particle size or number-average particle size which can range in particular from about 0.1 to 100 $\mu$m, preferably from 0.5 to 50 $\mu$m, preferably from 1 to 10 $\mu$m, this particle size being measured using a "Microtrac X100 & SRA 150" machine obtained from Leeds-Northrup.

Suitable electrolytes which can be used in the composition of the invention include, in particular, salts of mono-, di- or trivalent metals, more particularly salts of alkaline earth metals and in particular barium, calcium and strontium salts, salts of alkali metals and, for example, sodium and potassium salts, as well as magnesium, beryllium, yttrium, lanthanum, cerium, praseodymium, neodymium, promethium, samarium, europium, gadolinium, terbium, dysprosium, holmium, erbium, thulium, ytterbium, lutetium, lithium, tin, zinc, manganese, cobalt, nickel, iron, copper, rubidium, aluminum, silicon and selenium salts, and mixtures thereof.

The anions constituting these salts can be selected, for example, from carbonates, bicarbonates, sulfates, glycerophosphates, borates, chlorides, nitrates, acetates, hydroxides and persulfates, as well as the salts of α-hydroxy acids such as citrates, tartrates, lactates and malates or of fruit acids, or alternatively the salts of amino acids such as aspartate, arginate, glycocholate and fumarate.

Preferably, the salt is selected from calcium, magnesium, sodium and potassium salts and mixtures thereof, and more particularly magnesium chloride, potassium chloride, sodium chloride, calcium chloride and magnesium bromide, and mixtures thereof. It can be, in particular, a mixture comprising approximately from 6 to 10% of magnesium, from 11 to 15% of potassium, from 1 to 5% of sodium, up to 0.5% of calcium, from 30 to 45% of chlorides and less than 0.1% of sulfates, the remainder being insoluble materials and water of recrystallization which represents approximately from 27 to 40% of the mixture, the mixture being referred herein as "Dead Sea salts" since it corresponds to the composition of the salts present in the waters of the Dead Sea.

The amount of electrolyte(s) in the powder of the invention can vary within a wide range depending on the desired objective. This amount can range, for example, from 0.1 to 40%, preferably from 5 to 25% by weight, relative to the total weight of the cosmetic or dermatologic powder.

The modified starch employed in the powder of the invention can be modified by one or more of the following reactions: pregelatinization, oxidation, crosslinking, esterification. More specifically, these reactions can be conducted in the following manner:

(a) pregelatinization: bursting the starch granules, for example, by drying and cooking in a drying drum;

(b) oxidation with strong oxidizing agents leading to the introduction of carboxyl groups into the starch molecule and to the depolymerization of the starch molecule, for example, by treating an aqueous starch solution with sodium hypochlorite;

(c) crosslinking with functional agents which are capable of reacting with the hydroxyl groups of the starch molecules, which will thus be linked together, for example, with glyceryl and/or phosphate groups;

(d) esterification in an alkaline medium in order to graft functional groups, in particular acetyl, hydroxyethyl, hydroxypropyl, carboxymethyl, octenylsuccinic, onto the starch.

Suitable modified starches which can be used of the invention, include, for example, starches esterified with octenylsuccinic anhydride, and more particularly "Aluminium Starch octenyl succinate" such as the product sold by National Starch under the name Dry-Flo, the cross-linked corn starch sold under the name Resistamyl E2 by Amylum; a potato starch esterified with a carboxymethyl group, sold under the name Supramyl P 60 by Amylum, a corn starch esterified with a hydroxypropyl group, sold under the name Merigel EF6 by Amylum; a pregelatinized starch modified with octenylsuccinic anhydride and then with a hydrophobic unit, sold under the name Natrosorb HFB by National Starch; and a cross-linked and acetylated corn starch sold by Cerestar under the name C* Flo 06205.

A preferred embodiment of the invention is the use of the starches identified as Dry-Flo and C* Flo 06205.

The oily phase contains at least one oil. The oil used can be selected from mineral oils such as liquid paraffin or liquid petroleum jelly; silicone oils such as volatile silicone oils, oils of plant origin, for example, sweet almond oil or apricot kernel oil; oils of animal origin and synthetic oils, and mixtures thereof. The oil(s) component is the major proportion of the oily phase and preferably ranges from 50 to 100% by weight, more preferably from 80 to 100% by weight, relative to the weight of the oily phase.

Fatty substances can be added to the oil(s), such as fatty acids, fatty alcohols; waxes such as waxes of animal origin, for instance beeswax, carnauba wax or candelilla wax; mineral waxes, for instance microcrystalline waxes, and synthetic waxes, for instance, polyethylene wax or silicone wax.

The oily phase constitutes from 30 to 90% by weight, preferably from 50 to 90% by weight, relative to the total weight of the powder.

The powder of the invention can also comprise one or more additives commonly used in the cosmetics and dermatological fields. Suitable additives which may be mentioned include, for example, cosmetic and dermatologically active agents, emulsifiers or surfactants, detergents, dyestuffs including pigments, abrasive agents, antioxidants or free-radical scavengers, fillers and fragrances. These additives can be present in an amount from 0 to 30% of the total weight of the cosmetic and dermatological powder, preferably from 0.5 to 15% of the total weight of the powder.

Suitable active agents which may be mentioned include, for example, antiacne agents, antimicrobial agents, antiperspirants, astringent agents deodorants, hair removing agents, external analgesics, hair conditioners, skin conditioners, antisun agents, vitamins, essential fatty acids, keratolytic agents, enzymes, moisturizers, anti-inflammatories, detergents or foaming agents, fragrances, inorganic or organic matt-effect fillers and depigmenting agents.

Advantageously, the powder of the invention comprises a medium which is physiologically acceptable to the skin, mucous membranes and/or keratin fibers (hair and eyelashes).

Still another aspect of the invention is the process of manufacturing the cosmetic or dermatological powder of the invention comprising at least one modified starch, an oily phase and an electrolyte. The process of the invention comprises (1) the preparation of an oil-in-water dispersion by mixing an oily phase comprising at least one oil into an aqueous phase comprising at least one modified starch and at least one electrolyte, the oily phase/starch weight ratio being greater than or equal to 1, and (2) the dehydration of the dispersion in order to obtain the powder.

The term dispersion is intended to refer to any oil-in-water dispersion or emulsion, i.e. any mixture of an oily phase in an aqueous phase in the presence or absence of an emulsifier.

The aqueous phase of the oil-in-water dispersion preferably is at least 30% by weight of the dispersion. The aqueous phase generally comprises demineralized water. However, in the context of the present invention, some or all of this water can be replaced with a thermal or mineral water. In general, a mineral water is suitable for consumption, which is not always the case for a thermal water. Each of these waters contains, inter alia, trace elements and dissolved minerals. Suitable thermal or mineral waters which can be used include, for example, eau de Vittel, eaux du bassin de Vichy, eau d'Uriage, eau de la Roche Posay, eau de la Bourboule, eau d'Enghien-les-bains, eau de Saint-Gervais-les-bains, eau de Neris-les-bains, eau d'Allevard-les-bains, eau de Digne, eau des Maizieres, eau de Neyrac-les-bains, eau de Lons le Saunier, Eaux Bonnes, eau de Rochefort, eau de Saint Christau, eau des Fumades and eau de Tercis-les-bains.

The oily phase/starch weight ratio is generally greater than or equal to 1, and preferably ranges from 1 to 19, preferably from 2 to 10.

According to one specific embodiment of the process, the dispersion used is one which has a solids content ranging from 5 to 70% by weight and preferably ranging from 10 to 60% by weight. Such a solids content makes it possible for the dispersion to have a viscosity such that it is fluid enough to be useable in the remainder, of the steps.

The aqueous phase can be prepared at any temperature, typically from 0 to 100° C. The process is preferably conducted at a temperature ranging from 80° C. to 100° C.

In parallel, the oily phase is prepared and is added to the aqueous phase which is preferably cooled to a temperature below 80° C., preferably in an amount such that the resulting dispersion has a solids content ranging from 5 to 70% by weight relative to the total weight of the dispersion.

The dispersion is then formed by mixing the aqueous and oily phases slowly, for example, by gently incorporating the oily phase into the aqueous phase while maintaining constant stirring.

The oil-in-water dispersion is thus obtained with a pH which depends on its composition, but generally ranges from pH 4 to 9.

The process preferably comprises a homogenization step between the preparation of the dispersion, by mixing the oily phase and the aqueous phase, and before the dehydration of the dispersion obtained. The homogenization is advantageously conducted at high pressure, in order to reduce the average size of the droplets of the oily phase to about 350 nm or even less. The homogenization is conducted at a pressure generally ranging from 300 to 600 bar, preferably about 600 bar ($60 \times 10^6$ Pa), in order to obtain droplets of oily phase with an average size (on a number basis) preferably of less than 350 nm, generally ranging from 80 to 300 nm.

The dispersion thus homogenized is then dehydrated by any known process, and in particular by spraying or by freeze-drying. According to a preferred embodiment of the invention, the dehydration is conducted by spraying. In this case, the temperature of the hot air employed for drying preferably ranges from about 100° C. to 220° C. and the outlet temperature of the powder preferably ranges from about 30° C. to 140° C. The spraying time is very short, preferably less than or equal to 2 minutes.

Still a further aspect of the present invention is a powder, in particular a cosmetic and/or dermatological powder, which is prepared by the process described above.

The powder of the invention can be compacted in order to save volume and to make it easier to package, preserve, store and use. Before the optional compacting of the powder, the powder can undergo an additional granulation step with the objective to homogenize the particle size of the powder.

The powder of the invention has the advantage of being very stable and can be stored for several months without any phase separation, change in color, uptake of water, or other deterioration, for example, microbiological deterioration, being observed.

If the powder is incorporated into a composition, the composition preferably comprises an aqueous phase. Such an aqueous phase can be, for example, a lotion, a water-in-oil (W/O) emulsion, an oil-in-water (O/W) emulsion or alternatively a triple emulsion such as a water-in-oil-in-water (W/O/W) or oil-in-water-in-oil (O/W/O) emulsion, the amount of powder incorporated preferably ranging from 1 to 50%, preferably from 10 to 40% by weight relative to the total weight of the composition. The term "emulsion" here means both emulsifier-free dispersions and dispersions comprising emulsifiers, or alternatively dispersions stabilized with lipid spherules of the ionic or nonionic type.

The amount of electrolyte(s) in such a composition normally ranges, for example, from 2 to 15%, preferably from 3 to 8% by weight relative to the total weight of the composition.

These compositions are intended for topical application and appropriately comprise a medium which is physiologically acceptable to the skin, mucous membranes and/or keratin fibers (hair and eyelashes).

When the composition is an emulsion, this emulsion conventionally contains at least one oil and optionally a suitable emulsifier.

The nature of the emulsifier(s) employed depends on the type of emulsion which is desired. Suitable emulsifiers include, for example are (non)oxyethylenated fatty acid esters of polyols, such as sucrose stearate and sorbitan stearate. The emulsifier(s) can be present in the composition of the invention in a concentration which can vary within a wide range. Normally, the amount of emulsifier ranges, for example, from 0.1 to 20%, preferably from 1 to 5%, of the total weight of the composition.

The nature of the oily phase which forms part of the composition of the emulsions is not critical and may be any fatty substance conventionally used in cosmetics and dermatology, and in particular the oils indicated above. The oily phase of the emulsion can represent from 1 to 50%, preferably from 5 to 40% by weight relative to the total weight of the emulsion.

In addition, in a known manner, embodiments of the composition of the invention may contain adjuvants that are common in cosmetics and dermatology, such as hydrophilic or lipophilic active agents, preserving agents, antioxidants, fragrances, fillers, dyestuffs (pigments or dyes) and sunscreens, as well as lipid vesicles. These adjuvants are used in the usual cosmetic or dermatological amounts, for example, from 0.01 to 20% of the total weight of the emulsion, and, depending on their nature, the adjuvants are introduced into the aqueous phase or into the oily phase of the composition, or alternatively into vesicles.

Depending on the fluidity of the composition desired, one or more gelling agents may be added thereto, such as clays, polysaccharide gums and derivatives thereof such as xanthan gum and carboxymethyl hydroxypropyl guar, carboxyvinyl polymers or carbomers such as the products sold under the name Carbopol manufactured by Goodrich. These gelling agents are generally used at concentrations ranging from 0.1 to 10%, preferably 0.1 to 5%, more preferably from 0.1 to 3%, of the total weight of the composition.

The amounts of the various constituents in the compositions of the invention are those conventionally used in the sectors under consideration. The nature of the adjuvants and the amounts thereof must be such that they do not modify the properties of the compositions of the invention.

The subsequent use of the powder of the invention or of the composition containing it depends on the desired objective and on the active agents which may be present. The powder of the invention or the composition containing such a powder can be used in particular for the treatment and care of the skin, mucous membranes, the scalp and/or the hair, in particular for the treatment of sensitive skin and sensitive scalps and/or for moisturizing the skin as well as for the treatment of skin disorders such as dry skin, psoriasis, atopic dermatitis, vitiligo and fungal mycosis.

Thus, an aspect of the present invention is the cosmetic use of the powder or the composition as defined above, for treating sensitive skin and/or sensitive scalps and/or for moisturizing the skin. For more extensive details regarding sensitive skin, reference may be made to EP-A-680,749.

A further aspect of the present invention is the use of the powder or the composition as defined above for the manufacture of a dermatological composition intended for treating skin disorders, and in particular dry skin, psoriasis, atopic dermatitis, vitiligo and fungal mycosis.

Having now generally described the invention, a further understanding can be obtained by reference to certain specific Examples which are provided herein for purpose of illustration only and are not intended to be limiting unless otherwise specified.

The amounts of ingredients presented in the Examples are given as % by weight.

EXAMPLES

Example 1

Skincare Powder

| | |
|---|---|
| Modified starch (Dry Flo) | 18.2% |
| Apricot oil | 60.6% |
| Dead Sea salts (with 37.5% water of recrystallization) | 21.2% |

Procedure

A mixture containing 6% modified starch, 7% salts and 67% water is prepared and is heated to 95° C. and then cooled to 70° C., after which 20% of the apricot oil is incorporated, while stirring constantly so as to prepare an oil-in-water dispersion. The dispersion is cooled to room temperature with stirring and is homogenized at a pressure of about 600 bar ($60 \times 10^6$ Pa), after which it is placed in a spraying machine through which hot air is passed at 150° C. and the outlet temperature is 80° C.

The powder can be used in its existing, nonreconstituted form, and constitutes a product which is effective for sensitive skin, irritated skin and greasy skin. Furthermore, the powder has the advantage of containing a large percentage of salts while at the same time maintaining a cosmetic look and feel despite these concentrations.

Example 2

O/W Emulsion

| | |
|---|---|
| Aqueous phase: | |
| Sucrose stearate | 3.6% |
| Glycerol | 3% |
| Preserving agent | 0.25% |
| Water | 43.5% |
| Fatty phase | |
| Sorbitan stearate | 2.4% |
| Liquid fraction of karite butter | 5% |
| Volatile silicone oil | 12% |
| Xanthan gum | 0.2% |
| Carbopol | 0.05% |
| pH adjustment | |
| Sodium hydroxide | qs pH 5.8 |
| Incorporation of active agent | |
| Powder of Example 1 | 30% |

Procedure

The aqueous phase and the fatty phase are heated separately to 80° C. The fatty phase is then poured into the aqueous phase with vigorous stirring, after which the pH is adjusted with sodium hydroxide. After allowing the mixed composition to cool to about 40° C., the powder of Example 1 is added with gentler stirring.

A stable emulsion which is pleasant to use and capable of treating sensitive skin is obtained.

The disclosure of French priority Application No. 9814029, filed Nov. 6, 1998 is hereby incorporated by reference into the present application.

Obviously, numerous modifications and variations of the present invention are possible in light of the above teachings. It is therefore to be understood that within the scope of the appended claims, the invention may be practiced otherwise than as specifically described herein.

What is claimed as new and is intended to be secured by Letters Patent is:

1. A cosmetic or dermatological powder, which comprises:
   (i) from 5 to 60% by weight, relative to the total weight of the powder, of at least one starch modified by pregelatinization, oxidation, crosslinking, esterification or a combination thereof, (ii) from 30 to 90% by weight, relative to the total weight of the powder, of an oily phase comprising at least one oil, and (iii) at least one electrolyte, wherein the oily phase/starch weight ratio is $\geq 1$.

2. The powder according to claim 1, which is free of protein.

3. The powder according to claim 1, which comprises from 5 to 50% by weight, relative to the total weight of the powder, of at least one modified starch, from 0.1 to 40% by weight, relative to the total weight of the powder, of at least one electrolyte, and from 50 to 90% by weight, relative to the total weight of the powder, of an oily phase comprising at least one oil.

4. The powder according to claim 3, wherein the modified starch is starch esterified with octenylsuccinic anhydride.

5. The powder according to claim 1, wherein the oily phase comprises at least one oil selected from the group consisting of mineral oils, silicone oils, oils of plant origin, and oils of animal origin and synthetic oils.

6. The powder according to claim 1, wherein the oily phase also contains at least one fatty substance selected from the group consisting of fatty acids, fatty alcohols and waxes.

7. The powder according to claim 1, wherein the amount of electrolyte(s) ranges from 0.1 to 40% by weight relative to the total weight of the powder.

8. The powder according to claim 1, wherein the electrolyte is a salt of a mono-, di- or trivalent metal.

9. The powder according to claim 8, wherein the salt is selected from the group consisting of barium, calcium, strontium, sodium, potassium, magnesium, beryllium, yttrium, lanthanum, cerium, praseodymium, neodymium, promethium, samarium, europium, gadolinium, terbium, dysprosium, holmium, erbium, thulium, ytterbium, lutetium, lithium, tin, zinc, manganese, cobalt, nickel, iron, copper, rubidium, aluminum, silicon and selenium salts, and mixtures thereof.

10. The powder according to claim 9, wherein the anion of the electrolyte salt consists of ions selected from the group consisting of chloride, borate, bicarbonate, carbonate, nitrate, hydroxide, sulfate, persulfate, glycerophosphate and acetate ions, and anions of α-hydroxy acids, of fruit acids and of amino acids.

11. The powder according to claim 1, wherein the electrolyte is selected from the group consisting of calcium, magnesium or strontium nitrate, calcium or magnesium borate, calcium, magnesium, sodium, strontium, neodymium or manganese chloride, magnesium or calcium sulfate, calcium or magnesium acetate, and mixtures thereof.

12. The powder according to claim 1, which further comprises at least one additive selected from the group consisting of cosmetic or dermatological active agents, emulsifiers, detergents, dyestuffs, abrasive agents, antioxidants, free-radical scavengers, fragrances and fillers.

13. A process for manufacturing a cosmetic and/or dermatological powder, comprising:

preparing an oil-in-water dispersion by mixing an oily phase comprising at least one oil into an aqueous phase comprising at least one modified starch and at least one electrolyte, the oily phase/starch weight ratio being greater than or equal to 1; and dehydrating the dispersion in order to obtain the product powder.

14. The process according to claim 13, wherein the aqueous phase of the oil-in water dispersion represents at least 30% of the total weight of the dispersion.

15. The process according to claim 13, which further comprises, after preparing said dispersion, homogenizing the dispersion prior to drying the dispersion.

16. The process according to claim 15, wherein the homogenization is conducted at a pressure of about 600 bar.

17. The process according to claim 13, wherein the dehydration is conducted by spraying the dispersion.

18. The process according to claim 17, wherein the dehydration is conducted in a spraying machine in which the temperature of the hot air employed for the drying ranges from about 100° C. to 220° C. and the outlet temperature of the powder ranges from about 30° C. to 140° C.

19. A cosmetic and/or dermatological powder prepared by the process according to claim 13.

20. A cosmetic and/or dermatological composition, which comprises the powder according to claim 1.

21. The composition according to claim 20, which comprises at least one aqueous phase.

22. The composition according to claim 20, wherein the amount of powder ranges from 1 to 40% by weight relative to the total weight of the composition.

23. The composition according to claim 21, wherein the amount of powder ranges from 1 to 40% by weight relative to the total weight of the composition.

24. The composition according to claim 20, which contains from 2 to 15% by weight of electrolyte(s) relative to the total weight of the composition.

25. The composition according to claim 22, which contains from 2 to 15% by weight of electrolyte(s) relative to the total weight of the composition.

26. The composition according to claim 20, which is in the form of a lotion, a water-in-oil emulsion, an oil-in-water emulsion or a triple emulsion.

27. A cosmetic and/or dermatological composition, which comprises the powder according to claim 19.

28. The composition according to claim 27, which comprises at least one aqueous phase.

29. The composition according to claim 28, wherein the amount of powder ranges from 1 to 40% by weight relative to the total weight of the composition.

30. The composition according to claim 29, which contains from 2 to 15% by weight of electrolyte(s) relative to the total weight of the composition.

31. A method of treating sensitive skin and/or sensitive scalps and/or for moisturizing the skin, comprising:

applying the cosmetic powder according to claim 1 to sensitive skin and/or sensitive scalps.

* * * * *